(12) United States Patent
Liou et al.

(10) Patent No.: US 10,582,854 B2
(45) Date of Patent: Mar. 10, 2020

(54) TEMPERATURE SENSOR FOR MEASURING THERMISTOR RESISTANCE

(71) Applicant: Vital Connect, Inc., Campbell, CA (US)

(72) Inventors: Raymond Liou, Cupertino, CA (US); Arshan Aga, Mountain View, CA (US); Steve Fang, Sunnyvale, CA (US)

(73) Assignee: Vital Connect, Inc., San Jose, CA (US)

( * ) Notice: Subject to any disclaimer, the term of this patent is extended or adjusted under 35 U.S.C. 154(b) by 0 days.

(21) Appl. No.: 15/229,600

(22) Filed: Aug. 5, 2016

(65) Prior Publication Data

US 2018/0035889 A1  Feb. 8, 2018

(51) Int. Cl.
| | |
|---|---|
| *G01K 7/16* | (2006.01) |
| *A61B 5/00* | (2006.01) |
| *A61B 5/01* | (2006.01) |
| *G01K 1/02* | (2006.01) |
| *G01K 7/24* | (2006.01) |

(52) U.S. Cl.
CPC .............. *A61B 5/0008* (2013.01); *A61B 5/01* (2013.01); *G01K 1/024* (2013.01); *G01K 7/24* (2013.01); *A61B 2562/0276* (2013.01)

(58) Field of Classification Search
CPC ............ G01K 7/16; G01K 15/00; G01K 7/22; G01K 13/02; G01N 25/4813
USPC ................ 702/99; 340/870.17; 600/474, 549
See application file for complete search history.

(56) References Cited

U.S. PATENT DOCUMENTS

| | | | | |
|---|---|---|---|---|
| 5,072,097 A | * | 12/1991 | Miller ................... | B29C 65/20 156/359 |
| 5,081,988 A | * | 1/1992 | Cook .................. | A61N 1/3655 607/21 |
| 5,864,282 A | * | 1/1999 | Hannigan ............... | G01K 7/16 174/74 A |
| 6,553,336 B1 | * | 4/2003 | Johnson ................ | G01D 3/022 702/108 |
| 6,617,994 B1 | * | 9/2003 | Helm et al. ............ | H03M 1/12 341/172 |

(Continued)

FOREIGN PATENT DOCUMENTS

DE  102014107504 A  *  12/2014
JP  354161381 A  *  12/1979

*Primary Examiner* — Gail Kaplan Verbitsky
(74) *Attorney, Agent, or Firm* — Brundidge & Stanger, P.C.

(57) ABSTRACT

A method and system for determining thermistor resistance have been disclosed. The method comprises providing a temperature sensor network within a wireless sensor device, wherein the temperature sensor network includes a driver device and a receiver device, coupling the driver device to the receiver device using a dual bond wire system, determining at least one output voltage using at least one input current flowing through the dual bond wire system, and determining the thermistor resistance using the at least one output voltage. The system comprises a wireless sensor device including a temperature sensor network that comprises driver and receiver devices, and a dual bond wire system that couples the driver device to the receiver device, wherein at least one output voltage is determined using at least one input current flowing through the dual bond wire system, further wherein the thermistor resistance is determined using the at least one output voltage.

17 Claims, 7 Drawing Sheets

(56) References Cited

U.S. PATENT DOCUMENTS

| | | | | |
|---|---|---|---|---|
| 6,784,824 B1* | 8/2004 | Quinn | G06G 7/14 | 341/120 |
| 6,806,808 B1* | 10/2004 | Watters | G01D 5/48 | 340/10.41 |
| 7,367,712 B2* | 5/2008 | Becker | G01K 7/20 | 327/512 |
| 7,369,458 B2* | 5/2008 | Sifferman | G01S 7/524 | 367/13 |
| 7,743,266 B2* | 6/2010 | Chapuis | H02M 3/157 | 323/234 |
| 8,182,139 B2* | 5/2012 | Fiennes | G01K 15/00 | 374/1 |
| 8,192,080 B2* | 6/2012 | Clothier | B01J 3/04 | 340/584 |
| 8,376,611 B2* | 2/2013 | Li | G01K 7/22 | 327/513 |
| 8,540,644 B2* | 9/2013 | Husheer | A61B 5/0008 | 374/100 |
| 8,588,284 B2* | 11/2013 | Lakkis | A61B 5/00 | 375/219 |
| 8,729,977 B2* | 5/2014 | Filipovic | H03L 1/022 | 331/158 |
| 8,920,026 B2* | 12/2014 | Lazarov | G01R 19/00 | 374/1 |
| 8,931,950 B2* | 1/2015 | King | G01K 17/006 | 374/121 |
| 9,148,166 B2* | 9/2015 | Narayan | H03M 1/0604 | |
| 9,200,968 B2* | 12/2015 | Coln | G01K 7/186 | |
| 9,347,836 B2* | 5/2016 | Temkine | G01K 7/01 | |
| 9,347,837 B2* | 5/2016 | Kirkpatrick | G01K 13/00 | |
| 9,470,585 B2* | 10/2016 | Hong | G01K 7/16 | |
| 2004/0105488 A1* | 6/2004 | Felder | G01K 7/22 | 374/170 |
| 2007/0205916 A1* | 9/2007 | Blom | G01K 7/01 | 340/870.17 |
| 2008/0279255 A1* | 11/2008 | Burmeister | G01K 7/20 | 374/185 |
| 2009/0141767 A1* | 6/2009 | Cummins | G01N 27/223 | 374/142 |
| 2010/0040191 A1* | 2/2010 | Ubarretxena Belandia | G01K 1/024 | 377/25 |
| 2010/0082285 A1* | 4/2010 | Casasso | G01K 13/02 | 702/133 |
| 2010/0322283 A1* | 12/2010 | Clothier | G01K 7/36 | 374/176 |
| 2011/0291807 A1* | 12/2011 | Law | G01K 7/01 | 340/10.1 |
| 2011/0292967 A1* | 12/2011 | Parmet | G01K 7/25 | 374/170 |
| 2012/0051399 A1* | 3/2012 | Rud | G01K 7/20 | 374/185 |
| 2012/0161741 A1* | 6/2012 | Zambetti | G05F 3/262 | 323/294 |
| 2012/0226460 A1* | 9/2012 | Fiennes | G01K 15/00 | 702/99 |
| 2014/0343389 A1* | 11/2014 | Goldstein | A61B 5/0022 | 600/383 |
| 2015/0015281 A1* | 1/2015 | Bogner | G01K 7/20 | 324/705 |
| 2016/0167672 A1* | 6/2016 | Krueger | A61M 21/00 | 340/576 |
| 2016/0321222 A1* | 11/2016 | Greenberg | G06F 17/2247 | |

\* cited by examiner

TEMPERATURE SENSOR FOR MEASURING THERMISTOR RESISTANCE

FIELD OF THE INVENTION

The present invention relates to wearable sensor devices, and more particularly, to wearable sensor devices that include a temperature sensor for measuring thermistor resistance.

BACKGROUND

Wearable sensor devices are utilized to continuously monitor health related parameters (e.g., temperature) of a user. These wearable sensor devices include temperature sensors that utilize thermistors to measure the user's temperature. Conventional temperature sensors do not accurately measure the thermistor's resistance due to errors to offsets, current mismatches, gain variations, and digitization resolution limits that cause resistance measurements to vary greatly. Therefore, there is a strong need for a cost-effective and efficient solution that overcomes the aforementioned issues. The present invention addresses such a need.

SUMMARY OF THE INVENTION

A method and system for determining thermistor resistance have been disclosed. In a first aspect, the method comprises providing a temperature sensor network within a wireless sensor device, wherein the temperature sensor network includes a driver device and a receiver device, coupling the driver device to the receiver device using a dual bond wire system, determining at least one output voltage using at least one input current flowing through the dual bond wire system, and determining the thermistor resistance using the at least one output voltage.

In a second aspect, the system comprises a wireless sensor device including a temperature sensor network that comprises driver and receiver devices, and a dual bond wire system that couples the driver device to the receiver device, wherein at least one output voltage is determined using at least one input current flowing through the dual bond wire system, further wherein the thermistor resistance is determined using the at least one output voltage.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
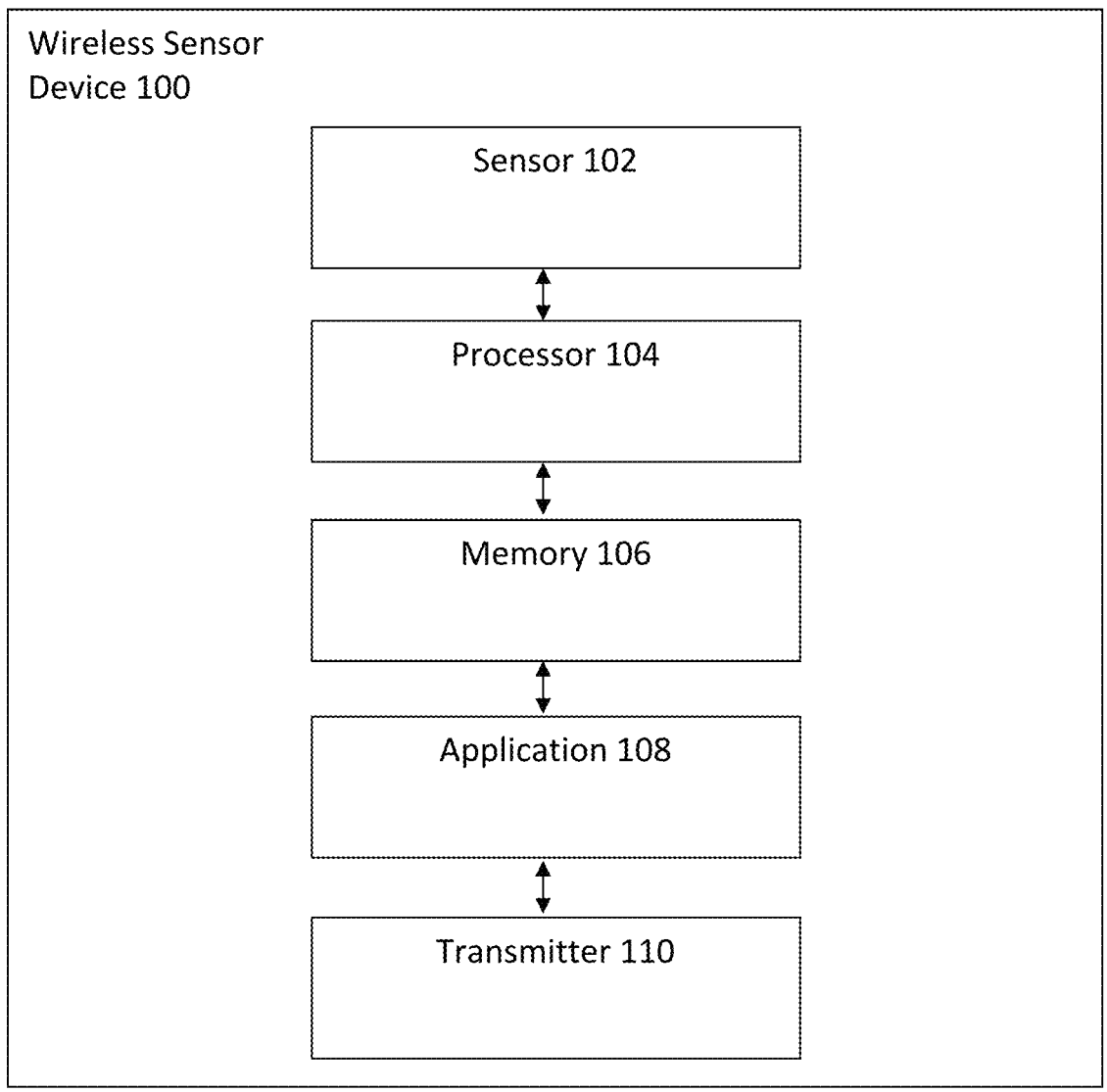
FIG. 1 illustrates a wireless sensor device in accordance with an embodiment.

The present invention relates to wearable sensor devices, and more particularly, to wearable sensor devices that include a temperature sensor for measuring thermistor resistance. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Wireless wearable sensor devices (wearable sensor devices) are utilized to continuously and/or remotely monitor the health of a user. Wearable sensor devices can include temperature sensors comprised of at least one thermistor to measure the temperature (e.g., body temperature, core temperature, etc.) of the user. A method and system in accordance with the present invention utilizes a temperature sensor application that provides extremely accurate measurements of a thermistor's resistance by eliminating errors due to offsets, current mismatches, gain variations, and digitization resolution limits that cause the thermistor's resistance measurements to vary greatly.

In the method and system in accordance with the present invention, the wearable sensor device utilizes a system that enables comparisons to a stable reference off chip resistor thereby eliminating the mismatch, gain variation, and offsets. Depending on the speed requirements of the device, a driver circuit design coupled with either a two-step or a four-step process for measuring the thermistor resistance is utilized to measure the thermistor's resistance. If system speed and power constraints are an issue, the less intensive two-step process (a first embodiment) can be utilized whereas if system speed and power constraints are not an issue, a more intensive four-step process can be utilized (a second embodiment).

In the first embodiment, the two-step process is cost-effective and enables elimination of input-referred offsets by utilizing comparisons with a reference resistor. In one embodiment, a variety of standard references resistors are utilized. However, the two-step process does not completely eliminate all mismatch and gain error problems. Therefore, in the second embodiment, for greater accuracy the four-step process is utilized which enables the elimination of input-referred offsets and further creates a ratio that cancels out mismatch and gain errors as well.

Digitization resolution of the analog-to-digital converter (ADC) of the wearable sensor device can also limit the accuracy of the final results and measurement of the thermistor's resistance. Therefore, in a third embodiment, the method and system in accordance with the present invention, includes a dithering process (after either the two-step or four-step process has been completed) that adds and subtracts voltages equal to fractions of the ADC's least significant bit (LSB). By adding these voltages and taking the average of the results, the method and system in accordance with the present invention effectively increases the resolution of the ADC.

For the most accurate measurement of the thermistor's resistance, the method and system in accordance with the present invention utilizes a fourth embodiment that combines all three of the aforementioned embodiments (first, second, third embodiments) together. The fourth embodiment is most accurate but is the slowest and requires the greatest amount of system bandwidth and power. However, faster but less accurate results can be obtained using a selection and/or a variety of combinations of the three aforementioned embodiments (e.g., two-step process only, four-step process only, two-step process plus dithering process, four-step process plus dithering process).

When connecting the off-chip thermistor and reference resistor, a dual-bond wire system is implemented by the method and system in accordance with the present invention so that the resistance of the dual-bond wire is not included when calculating total resistance of the thermistor thereby leading to an accurate thermistor resistance measurement. The current is sent through one bond wire of the dual-bond wire but is excluded when measuring the voltage through the other bond wire of the dual-bond wire. This results in a very accurate resistance measurement of the thermistor.

In one embodiment, a predetermined and predefined specifications table converts the thermistor resistance to the actual temperature detected. In another embodiment, the wearable sensor device utilizes a dynamically updated cloud based database that compares various thermistor resistances measured from a plurality of wearable sensor devices connected to the cloud based database at specific usage and/or activity time periods to generate the actual temperatures detected.

To describe the features of the present invention in more detail, refer now to the following description in conjunction with the accompanying Figures.

FIG. 1 illustrates a wireless sensor device 100 in accordance with an embodiment. In one embodiment, the wireless sensor device 100 is a wearable sensor device that utilizes a flexible circuit design in a patch form factor (i.e., the wearable device is a patch that adheres to the user to measure the user's vital body signs) that is either entirely disposable (both the adhesive patch portion and the electronic module and sensor device portion) or partially disposable (e.g., the electronic module and sensor device portion being reusable and the adhesive patch portion being disposable).

In one embodiment, the wireless sensor device 100 ("wearable device") includes at least one sensor 102, at least one processor 104 coupled to the at least one sensor 102, at least one memory 106 coupled to the at least one processor 104, at least one application 108 coupled to the at least one memory 106, and at least one transmitter 110 coupled to the at least one application 108. One of ordinary skill in the art readily recognizes that the wireless sensor device 100 can include other components not aforementioned and that the components of the wireless sensor device 100 can be coupled in a variety of different ways from the orientation shown in FIG. 1 and that would be within the spirit and scope of the present invention.

In one embodiment, the wireless sensor device 100 is attached to a user via an adhesive patch to detect various physiological signals including the user's temperature via the at least one sensor 102. The at least one sensor 102 obtains the physiological signal data (typically in raw format) from the user, which is transmitted to the at least one memory 106 and in turn to the at least one application 108 via the at least one processor 104. The at least one processor 104 executes the at least one application 108 to process, transform, and analyze the data to obtain critical health-related information of the user including but not limited to the user's temperature.

In one embodiment, the at least one application 108 utilizes embedded algorithms and processes to process, transform, and analyze the data. By executing the at least one application 108 to process the data detected by the at least one sensor 102, the overall functioning of the wireless sensor device 100 is improved and the technical field related to determining the user's temperature is also improved.

The information is transmitted to the at least one transmitter 110 and in turn relayed to another user or device for further processing, analysis, and storage. In another embodiment, the at least one transmitter 110 transmits the various physiological signals detected in raw form by the at least one sensor 102 to a remote device/server (e.g., smartphone, cloud-based server, etc.) for further processing, analysis, and storage.

In one embodiment, the at least one sensor 102 is any of a microelectromechanical systems (MEMS) multi-axial (e.g., tri-axial) accelerometer, an embedded sensor with electrodes, a temperature sensor, and a photoplethysmography sensor. In one embodiment, the at least one processor 104 is a microprocessor. One of ordinary skill in the art readily recognizes that a variety of device types and designs can be utilized for the at least one sensor 102, the at least one processor 104, the at least one memory 106, the at least one application 108, and the at least one transmitter 110 and that would be within the spirit and scope of the present invention.

In addition, one of ordinary skill in the art readily recognizes that a variety of wireless sensor devices can be utilized including but not limited to wearable sensor devices, a wireless sensor device in a patch form-factor, the Vital Connect HealthPatch® and/or VitalPatch® wearable devices, electrocardiograph devices, smart watches, photoplethysmographs, pulse oximeters, uni-axial accelerometers, bi-axial accelerometers, tri-axial accelerometers, gyroscopes, and pressure sensors and that would be within the spirit and scope of the present invention.

In one embodiment, the HealthPatch® and VitalPatch® wearable devices are disposable adhesive patch biosensors (either partially or fully disposable) worn on the user's chest or another location of the body. The wearable devices incorporate at least two surface electrodes with a hydrogel-like material on the bottom, at least one battery, at least one electronic module with an embedded processor and other electronic components and circuitry (that is reusable in the HealthPatch® and that is fully disposable in the VitalPatch®), at least one MEMS tri-axial accelerometer, and at least one Bluetooth Low Energy (BLE) transceiver.

In one embodiment, the wearable device facilitates continuous and automated monitoring of a plurality of physiological signals. In this embodiment, after the wearable device detects the plurality of physiological signals (in raw form) via a plurality of internal and embedded sensors, the electronic module of the wearable device utilizes a plurality of algorithms (e.g., firmware algorithms) and processing techniques to process and transform the raw waveforms of the plurality of physiological signals into actionable data outputs which are then transmitted as a stream of processed physiological variables via the BLE transceiver/link as encrypted data to a relay such as a smartphone, where the live (real-time) streams of data can be viewed, stored, and further processed/analyzed.

Figure 2:
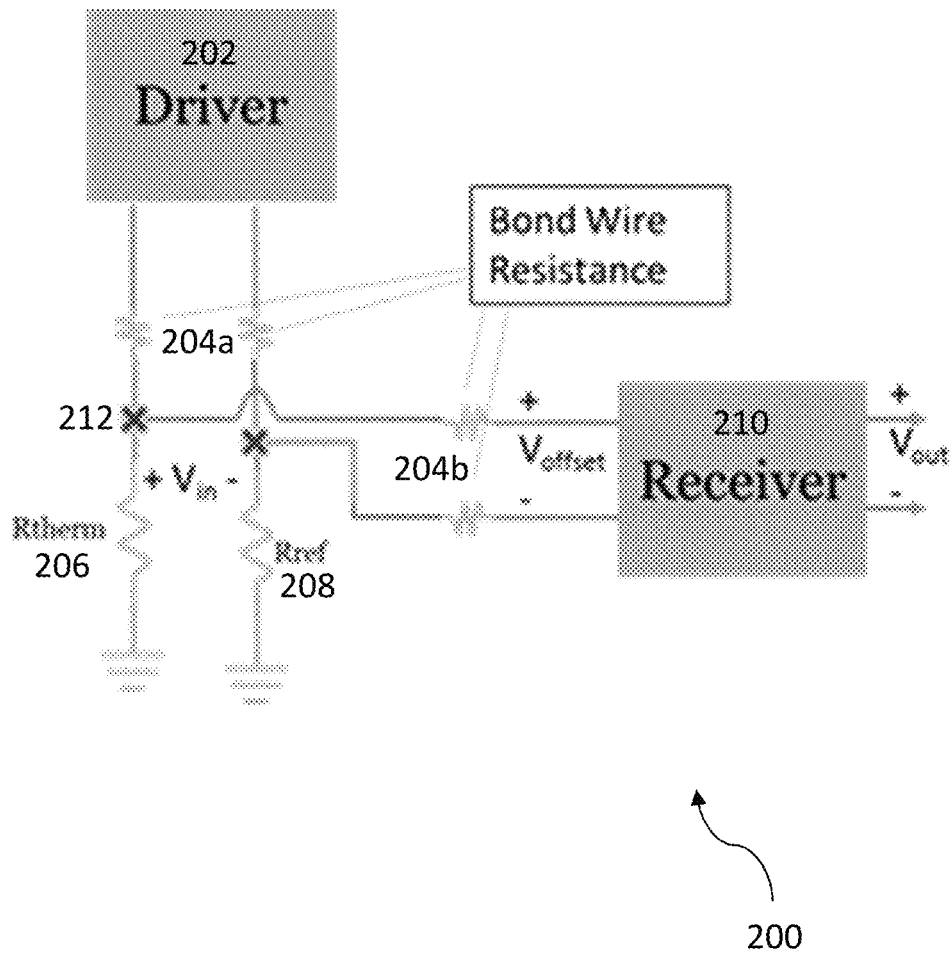
FIG. 2 illustrates a diagram of a temperature sensor network within a wireless sensor device in accordance with an embodiment.

FIG. 2 illustrates a diagram 200 of a temperature sensor network within a wireless sensor device in accordance with an embodiment. The temperature sensor network (or circuit chip) is part of the circuitry of a temperature sensor that is embedded within the wireless sensor device 100 (functioning as the at least one sensor 102). The diagram 200 includes a driver device/unit 202 and a receiver device/unit 210.

In FIG. 2, a dual bond wire mechanism and design comprising a first set of bond wires 204a and a second set of bond wires 204b is used to eliminate errors in resistance measurements. The first and second set of bond wires 204a-b connect to a same pin 212 of the chip package of the temperature sensor. In one embodiment, the resistance of the thermistor is more accurately determined using the temperature sensor network of FIG. 2 but in another embodiment, the resistance of different types of resistors is determined. Each of the first set and the second set of bond wires 204a-b have a bond wire resistance as denoted in FIG. 2.

By separating out the bond wires into the first set of bond wires 204a and the second set of bond wires 204b, electrical current that flows from the driver device/unit 202 is passed only through the first set of bond wires 204a but the receiver device/unit 210 measuring the voltage drop of the resistors ($R_{therm}$ 206 and $R_{ref}$ 208) does not measure the voltage drop of the first set of bond wires 204a. In one embodiment, each bond wire is between the pin 212 of the chip package and a pad on the chip die itself. Therefore, unlike conventional temperature sensors that utilize one pad per pin, the present invention utilizes two pads per pin and a connection process for finding the off chip voltage across the thermistor to ignore the bond wire resistances. In one embodiment, a 10 microamperes (10 uA) current output is sent through the resistors ($R_{therm}$ 206 and $R_{ref}$ 208) of the temperature sensor network/circuit from a current mirror. In another embodiment, output currents of varying levels are sent through the resistors.

As a result, the second set of bond wires 204b attached to the receiver device/unit 210 will not have an electrical current pass through which will not affect the captured voltage. Thus, the resistance of the second set of bond wires 204b is not included when calculating the total resistance of the thermistor. In one embodiment, the calculation is carried out by the receiver device/unit 210 using a processor, memory device coupled to the processor, and an application stored on the memory device which when executed by the processor carries out the resistance calculations. Accordingly, as aforementioned, the current is sent through the first set of bond wires 204a but is excluded when measuring the voltage through the second set of bond wires 204b thereby resulting in an accurate resistance measurement of the thermistor ($R_{therm}$ 206).

In one embodiment, the $R_{therm}$ 206 represents the resistance of an off chip thermistor and the $R_{ref}$ 208 represents the resistance of a stable reference off chip resistor. In this embodiment, the $v_{out}$ calculation of FIG. 2 is done before digitization (carried out by an analog-to-digital converter ADC that is not shown in FIG. 2 but would be attached/coupled after the receiver device/unit 210) and is calculated by multiplying the gain of the receiver device/unit 210 ($Gain_{receiver}$) with the summation of the input voltage ($v_{in}$ per FIG. 2) and the offset voltage ($v_{offset}$ per FIG. 2) per the following equation (1):

$$v_{out} = (v_{in} + v_{offset}) \times Gain_{receiver} \quad (1).$$

Figure 3:
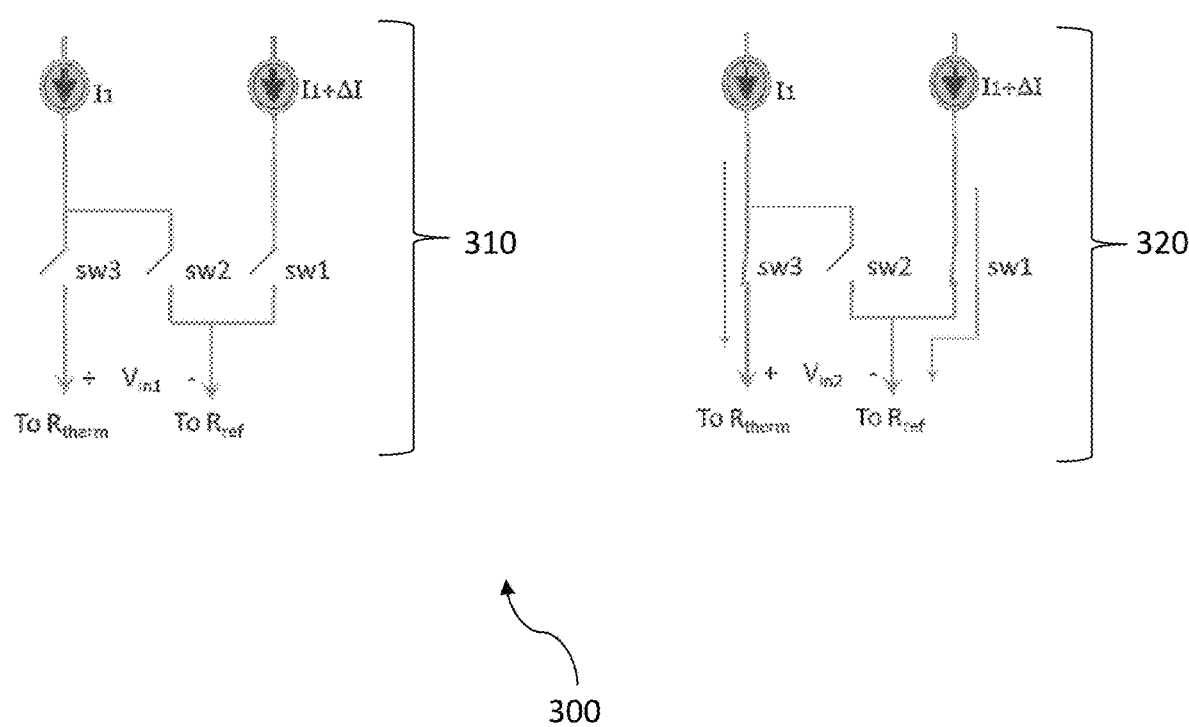
FIG. 3 illustrates a method for measuring thermistor resistance via a driver circuit in accordance with a first embodiment.

FIG. 3 illustrates a method 300 for measuring thermistor resistance via a driver circuit in accordance with a first embodiment. The driver circuit includes electrical current flow inputs via each of the separate bond wires (first current $I_1$ and second current $I_1 + \Delta I$), three switches (sw1, sw2, sw3), and electrical current flow outputs that flow towards the resistance of the thermistor ($R_{therm}$) and the reference resistance ($R_{ref}$). The driver circuit of FIG. 3 represents the driver device/unit 202 of the temperature sensor network illustrated by FIG. 2. Thus, the driver circuit is coupled to a receiver circuit (receiver device/unit 210) via the dual bond wire design as illustrated in FIG. 2 but not illustrated in FIG. 3. In one embodiment, the temperature sensor network is housed within the at least one sensor 102 module of the wireless sensor device 100.

The method 300 is a two-step process that comprises a first step 310 and a second step 320. In the first step 310, all three switches (sw1, sw2, sw3) are off (either turned off by the system to prepare for the two-step process or already in an off position) and so no current flows through $R_{therm}$ and $R_{ref}$. In the second step 320, the first switch (sw1) and the third switch (sw3) are both turned on (with the second switch sw2 not turned on by the wearable sensor device and thus remaining off). Therefore, the first current $I_1$ flows towards $R_{therm}$ and the second current $I_1 + \Delta I$ flows towards $R_{ref}$.

In FIG. 3, the two-step process of method 300 results in two different output voltage calculations ($v_{out}$) according to each step (the first step 310 and the second step 320) of the two-step process. After the first step 310, the first output voltage ($v_{out1}$) is calculated as the offset voltage ($v_{offset}$) multiplied by the gain of the receiver ($Gain_{receiver}$) per the following equation (2):

$$v_{out1} = v_{offset} \times Gain_{receiver} \quad (2).$$

After the second step 320 when the first (sw1) and third (sw3) switches are turned on and current is flowing through the driver circuit, the second output voltage ($v_{out2}$) is calculated as the gain of the receiver ($Gain_{receiver}$) multiplied by a value derived from taking the first current ($I_1$) multiplied by the thermistor resistance ($R_{therm}$) which is subtracted by the second current ($I_1 + \Delta I$) multiplied by the reference resistance ($R_{ref}$) which is added to the offset voltage ($v_{offset}$) per the following equation (3):

$$v_{out2} = [(I_1 \times R_{therm}) - ((I_1 + \Delta I) \times R_{ref}) + v_{offset}] \times Gain_{receiver} \quad (3).$$

The first and second output voltages are utilized by the at least one application 108 of the wireless sensor device 100 to calculate the total resistance of the thermistor which doesn't include the resistance of the dual bond wires. The total resistance of the thermistor ($R_t$) is calculated by subtracting the second output voltage ($v_{out2}$) by the first output voltage ($v_{out1}$) and dividing that resulting value by the product of the ideal current ($I_{ideal}$) and ideal gain ($Gain_{ideal}$). The total resistance of the thermistor calculation utilizes values for the first output voltage ($v_{out1}$) and the second output voltage ($v_{out2}$) from equations (2) and (3) per the following equation (4):

$$R_t = (v_{out2} - v_{out1}) / (I_{ideal} \times Gain_{ideal}) = [((I_1 \times (R_{therm} - R_{ref})) - (\Delta I \times R_{ref})) / I_{ideal}] \times [Gain_{receiver} / Gain_{ideal}] \quad (4).$$

The overall calculations related to equation (4) are shown below:

$$R_{Calculation} = \frac{(V_2 - V_1)}{I_{Ideal} Gain_{Ideal}} = \frac{I_1(R_{therm} - R_{ref}) - \Delta I R_{ref}}{I_{Ideal}} \times \frac{Gain_{Receiver}}{Gain_{Ideal}}$$

Figure 4:
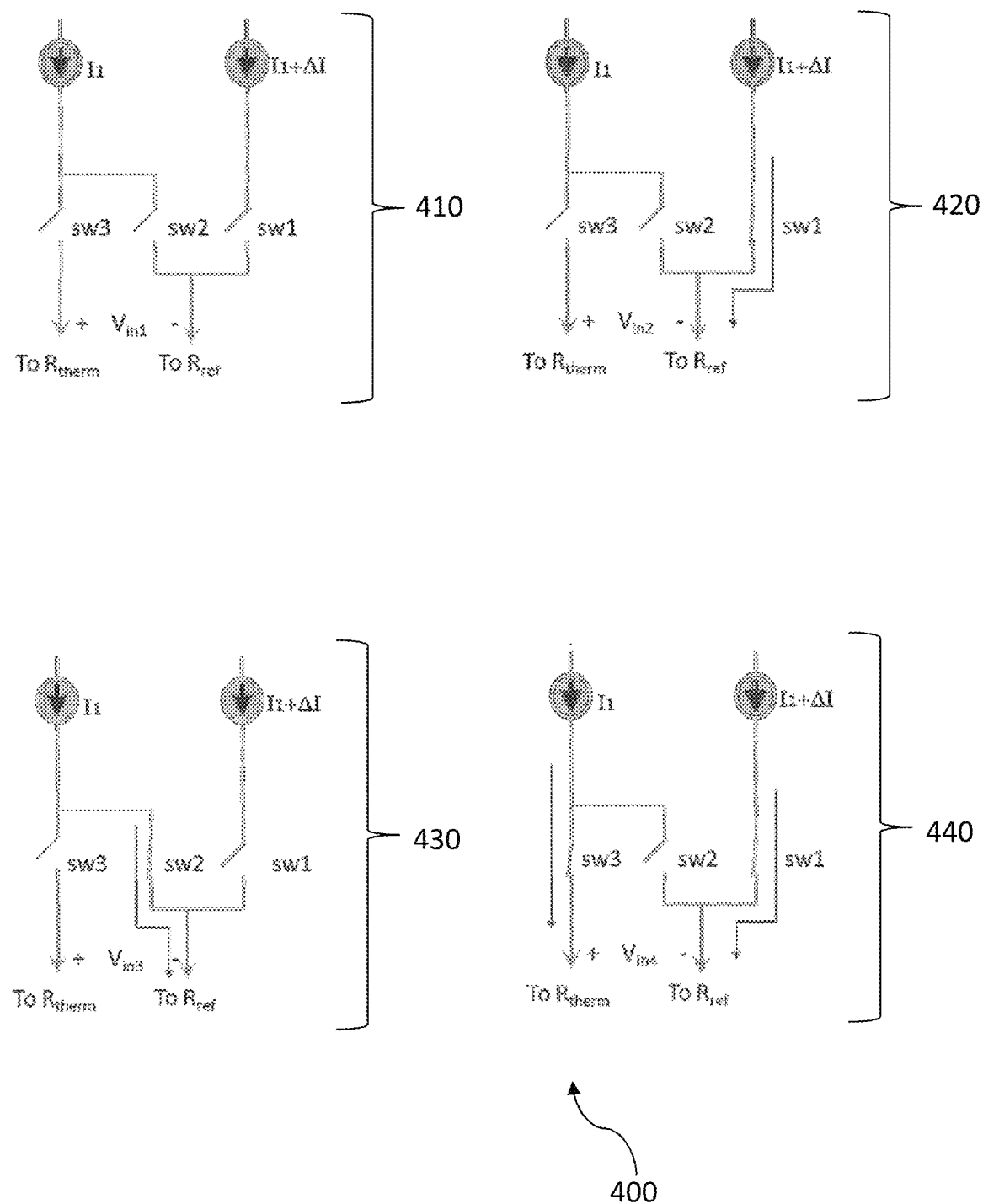
FIG. 4 illustrates a method for measuring thermistor resistance via a driver circuit in accordance with a second embodiment.

FIG. 4 illustrates a method 400 for measuring thermistor resistance via a driver circuit in accordance with a second embodiment. As in FIG. 3, the driver circuit includes electrical current flow inputs via each of the separate bond wires (first current $I_1$ and second current $I_1 + \Delta I$), three switches (sw1, sw2, sw3), and electrical current flow outputs that flow towards the resistance of the thermistor ($R_{therm}$) and the reference resistance ($R_{ref}$). The driver circuit of FIG. 4 represents the driver device/unit 202 of the temperature sensor network illustrated by FIG. 2. Thus, the driver circuit is coupled to a receiver circuit (receiver device/unit 210) via the dual bond wire design as illustrated in FIG. 2 but not illustrated in FIG. 4.

The method 400 is a four-step process that comprises a first step 410, a second step 420, a third step 430, and a fourth step 440. Comparatively, the four-step process deals with mismatch and gain error issues that may remain if the two-step process of FIG. 3 is only utilized by the wireless sensor device 100. The four-step process allows the elimination of input-referred offsets and creates a ratio that cancels out the mismatch and gain error issues.

Referring to FIG. 4, in the first step 410, as in the first step 310 of FIG. 3, all three switches (sw1, sw2, sw3) are off (either turned off by the system to prepare for the four-step process or already in an off position) and so no current flows through $R_{therm}$ and $R_{ref}$. In the second step 420, only the first switch (sw1) is turned on (with both the second switch sw2 and the third switch sw3 not turned on and thus remaining off). Therefore, after the second step 420, only the second current $I_1+\Delta I$ flows towards $R_{ref}$ and the first current $I_1$ does not yet flow towards $R_{therm}$.

Referring once again to FIG. 4, in the third step 430, only the second switch (sw2) is turned on (with the first switch sw1 being turned off and the third switch sw3 remaining off). Therefore, after the third step 430, only the first current $I_1$ flows towards $R_{ref}$. In the fourth step 440, as in the second step 320 of FIG. 3, the first switch (sw1) and the third switch (sw3) are both turned on (with the second switch sw2 being turned off). Therefore, the first current $I_1$ flows towards $R_{therm}$ and the second current $I_1+\Delta I$ flows towards $R_{ref}$.

In FIG. 4, the four-step process of method 400 results in four different output voltage calculations ($v_{out}$) according to each step (steps 410, 420, 430, and 440) of the four-step process. After the first step 410 of the method 400, similar to step 310 of FIG. 3, with no current flowing through the driver circuit, the first output voltage ($v_{out1}$) is calculated as the offset voltage ($v_{offset}$) multiplied by the gain of the receiver ($\text{Gain}_{receiver}$) per the following equation (5):

$$v_{out1} = v_{offset} \times \text{Gain}_{receiver} \quad (5).$$

After the second step 420 of the method 400, when only the first switch (sw1) is turned on and current is flowing through the reference resistor (with resistance $R_{ref}$) of the driver circuit, the second output voltage ($v_{out2}$) is calculated as the gain of the receiver ($\text{Gain}_{receiver}$) multiplied by a value derived from taking a negative value of the second current ($I_1+\Delta I$) multiplied by the reference resistance ($R_{ref}$) which is added to the offset voltage ($v_{offset}$) per the following equation (6):

$$v_{out2} = [-(I_1+\Delta I) \times R_{ref}) + v_{offset}] \times \text{Gain}_{receiver} \quad (6).$$

After the third step 430 of the method 400, when only the second switch (sw2) is turned on and current is flowing through the reference resistor (with resistance $R_{ref}$) of the driver circuit, the third output voltage ($v_{out3}$) is calculated as the gain of the receiver ($\text{Gain}_{receiver}$) multiplied by a value derived from taking a negative value of the first current ($I_1$) multiplied by the reference resistance ($R_{ref}$) which is added to the offset voltage ($v_{offset}$) per the following equation (7):

$$v_{out3} = [(-I_1 \times R_{ref}) + v_{offset}] \times \text{Gain}_{receiver} \quad (7).$$

After the fourth step 440 of the method 400, similar to the second step 320 of FIG. 3, when the first (sw1) and third (sw3) switches are turned on and current is flowing through both the thermistor (with resistance $R_{therm}$) and the reference resistor (with resistance $R_{ref}$) of the driver circuit, the fourth output voltage ($v_{out4}$) is calculated as the gain of the receiver ($\text{Gain}_{receiver}$) multiplied by a value derived from taking the first current ($I_1$) multiplied by the thermistor resistance ($R_{therm}$) which is subtracted by the second current ($I_1+\Delta I$) multiplied by the reference resistance ($R_{ref}$) which is added to the offset voltage ($v_{offset}$) per the following equation (8):

$$v_{out2} = [(I_1 \times R_{therm}) - ((I_1+\Delta I) \times R_{ref}) + v_{offset}] \times \text{Gain}_{receiver} \quad (8).$$

The aforementioned first, second, third, and fourth output voltages resulting from the four-step process of the method 400 are utilized by the at least one application 108 of the wireless sensor device 100 to calculate the total resistance of the thermistor which doesn't include the resistance of the dual bond wires. The total resistance of the thermistor ($R_t$) is calculated by subtracting the fourth output voltage ($v_{out4}$) by the second output voltage ($v_{out2}$) and dividing that resulting value by the difference between the first and third output voltages ($v_{out1}$ and $v_{out3}$ respectively) and then multiplying this resulting value by the reference resistance ($R_{ref}$). Therefore, the total resistance of the thermistor calculation utilizes values for the first output voltage ($v_{out1}$), second output voltage ($v_{out2}$), third output voltage ($v_{out3}$), and fourth output voltage ($v_{out4}$), from equations (5), (6), (7), and (8) per the following equation (9):

$$R_t = [(v_{out4} - v_{out2})/(v_{out1} - v_{out3})] \times R_{ref} \quad (9).$$

By plugging in these values, equation (9) is reduced to equaling the reference resistance ($R_{ref}$) multiplied by the value derived from multiplying the first current ($I_1$) by the thermistor resistance ($R_{therm}$) and dividing that resulting value by the first current ($I_1$) multiplied by the reference resistance ($R_{ref}$) per the following equation (10):

$$R_t = [(I_1 \times R_{therm})/(I_1 \times R_{ref})] \times R_{ref} \quad (10).$$

Equation (10) further reduces to $R_{therm}$ as the mismatch and gain errors are cancelled out. The overall calculations relating to equation (10) are shown below:

$$\begin{aligned} R_{Calculation} &= \frac{V_{out4} - V_{out2}}{V_{out1} - V_{out3}} \times R_{ref} \\ &= \frac{[I_1 \times R_{therm} + V_{offset} - (I_1 + \Delta I) \times R_{ref} + (I_1 + \Delta I) \times R_{ref} - V_{offset}] \times \text{Gain}_{Receiver}}{(V_{offset} + I_1 \times R_{ref} - V_{offset}) \times \text{Gain}_{Receiver}} \\ &= \frac{I_1 \times R_{therm}}{I_1 \times R_{ref}} \times R_{ref} \\ &= R_{therm} \end{aligned}$$

In one embodiment, an additional dithering process is utilized and added at the amplifier stage to improve quantization noise (by increasing the resolution of the ADC by breaking down the least significant bit (LSB) by averaging dithered outputs) due to the analog-to-digital converter (ADC). The dithering process adds or subtracts small voltages to the amplified signal that covers at least the range of 1 least significant bit (LSB) of the ADC. Utilizing 1 LSB enables effective dithering because that is the desired break down range. By setting the range to be 1 LSB, the accuracy is increased by the number of steps in the dither of that LSB. After each dithering voltage step, the ADC captures and digitizes the new voltage.

The dithering voltage step is a fraction of the ADC's LSB such that after stepping through the full range, there is a LSB change at the output of the ADC for the same signal. In other words, each time you step in the dither process, the ADC calculates a new value (an ADC output value). The system provides the same amount of ADC outputs as dither steps. The ADC outputs are then averaged and the ADC outputs are between 1-2 different LSB values. Therefore, after averaging, the system determines how close to one LSB the input is compared to the other.

After all the dithering voltage steps have been captured, the resulting output is a combination of what the original digital output would be and digital outputs that are 1 LSB different. Averaging allows the determination of a more precise voltage measurement that would have been limited by the ADC digitization resolution. Accordingly, the amount of dithering steps that are added divide down the ADC's LSB resulting in an ADC with that smaller LSB. Thus, the dithering process artificially increases the number of bits of the ADC. Averaging the ADC output values not only increases the accuracy but also averages out any high frequency noise including but not limited to quantization noise.

In one embodiment, the dithering process uses 1/5 LSB with 5 steps of dithering but one of ordinary skill in the art readily recognizes that these numbers can be changed (e.g., utilizing more than 5 steps of dithering) for improved resolution and that would be within the spirit and scope of the present invention. The dithering process is an optional step that can be used at the end of either the two-step process (method 300 of FIG. 3) or the four-step process (method 400 of FIG. 4) to improve the accuracy of the thermistor's resistance determination.

Figure 5:
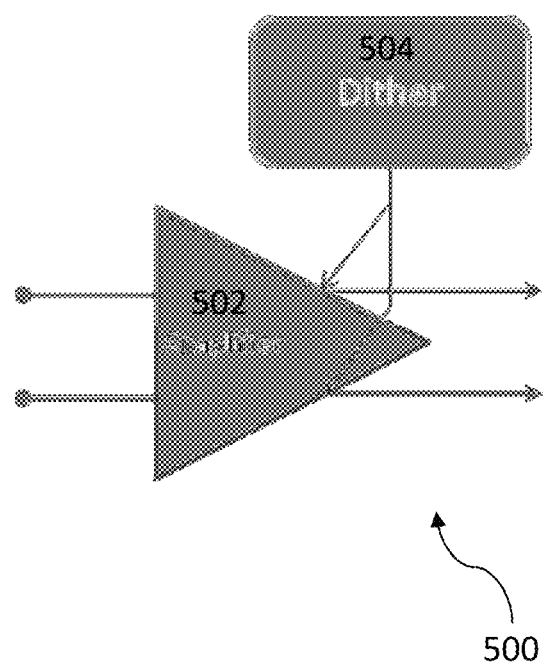
FIG. 5 illustrates a diagram of a dithering device in accordance with an embodiment.

FIG. 5 illustrates a diagram 500 of a dithering device in accordance with an embodiment. The digitization resolution of the ADC can also limit the accuracy of the final result/determination of the thermistor's resistance. The dithering device utilizes a dithering process that adds and subtracts voltages equal to fractions of the ADC's LSB. By adding/subtracting these voltages and taking the average of the results, the resolution of the ADC is increased. In one embodiment, the dithering process adds two additional device units or modules to the temperature sensor network of FIG. 2 which comprise an amplifier unit 502 coupled to a dithering process unit 504. As aforementioned, the dithering process can be utilized after the completion of the two-step or four-step processes described by FIGS. 3 and 4 respectively.

Therefore, in one embodiment, the amplifier unit 502 is coupled to the receiver device/unit 210 of FIG. 2 (which is not shown in FIG. 5) and receives an analog signal comprising the captured voltage outputs ($v_{out}$) determined using method 300 or 400 (depending on whether the two-step or four-step process was utilized). The dithering process is applied to the analog signal using the dithering unit 504 prior to the total resistance calculations and digitization (converting the signal from analog to digital) by the ADC.

Therefore, the dithering process steps are applied to the output voltages garnered from the aforementioned two-step process (method 300 of FIG. 3) and four-step process (method 400 of FIG. 4) but before the thermistor's resistance calculations are carried out by the wireless sensor device 100. In one embodiment, each output voltage value from either method 300 or method 400 is dithered immediately. In another embodiment, there is a predetermined delay prior to the dithering process. The dithering process results in an averaged output voltage that is a more precise voltage measurement that is not limited by the ADC digitization resolution.

Figure 6:
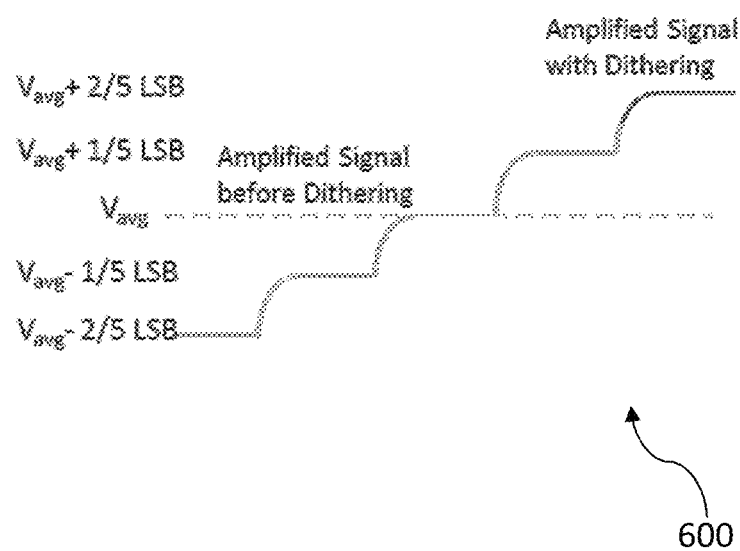
FIG. 6 illustrates a dithering process of an amplified signal in accordance with an embodiment.

FIG. 6 illustrates a dithering process 600 of an amplified signal in accordance with an embodiment. In FIG. 6, the dithering process 600 uses 1/5 LSB with 5 steps of dithering. In another embodiment, the dithering process 600 utilizes different LSB levels (e.g., 1/10 LSB) and different step numbers (e.g., 10 steps). If additional step numbers are utilized, additional system requirements are needed (i.e., the process is more costly) whereas if a lesser number of step numbers are utilized, less system requirements are needed (i.e., the process is less costly).

Figure 7:
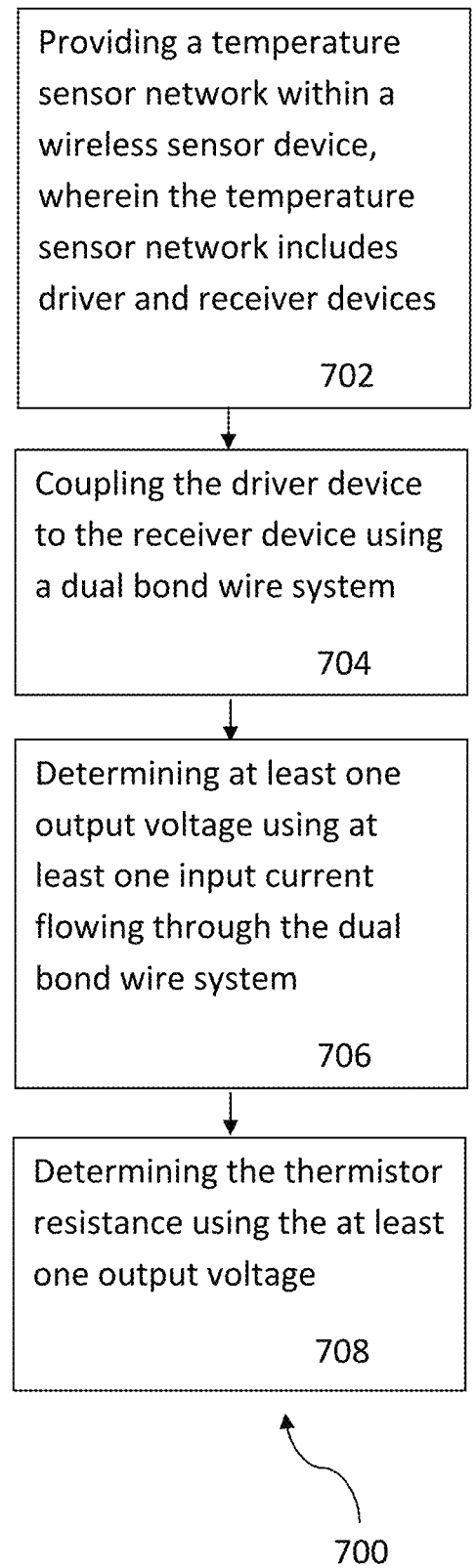
FIG. 7 illustrates a method for determining thermistor resistance in accordance with an embodiment.

FIG. 7 illustrates a method 700 for determining thermistor resistance in accordance with an embodiment. The method 700 comprises providing a temperature sensor network (or temperature sensor or temperature sensor circuit) within a wireless sensor device, wherein the temperature sensor network includes a driver device and a receiver device, coupling the driver device to the receiver device using a dual bond wire system, determining at least one output voltage using at least one input current flowing through the dual bond wire system, and determining the thermistor resistance using the at least one output voltage.

In one embodiment, the determining of the least one output voltage step is done prior to digitization by an analog-to-digital converter (ADC) coupled to the receiver device. The dual bond wire system comprises a first set of bond wires coupled to the driver device and a second set of bond wires coupled to the receiver device, further wherein the at least one input current passes through the first set of bond wires but does not pass through the second set of bond wires.

In one embodiment, one of the first set of bond wires is coupled to one of the second set of bond wires and the other of the first set of bond wires is coupled to the other of the second set of bond wires. In one embodiment, the method further comprises determining an input voltage using a plurality of switches across the first set of bond wires and measuring an offset voltage across the second set of bond wires.

In one embodiment, the plurality of switches comprises a first switch, a second switch, and a third switch. In another embodiment, the plurality of switches comprises a different number of switches. The output voltage is calculated as the value determining by adding the input voltage and the offset voltage together and then multiplying this resulting value by the gain of the receiver.

In one embodiment that utilizes the two-step process of FIG. 3, the input voltage comprises a first input voltage and a second input voltage. In this embodiment, the method further comprises determining the first input voltage when each of the first switch, the second switch, and the third switch are turned off (which results in no value for the first input voltage since no current can flow through to the thermistor and reference resistor when all the switches are off), and determining the second input voltage when both the first switch and the third switch are turned on, and when the second switch is turned off.

In this embodiment, the at least one output voltage comprises a first output voltage and a second output voltage. The first output voltage is determined using the first input voltage, the offset voltage, and a gain of the receiver device and the second output voltage is determined using the second input voltage, the offset voltage, and the gain of the receiver device.

In another embodiment that utilizes the four-step process of FIG. 4, the input voltage comprises a first input voltage, a second input voltage, a third input voltage, and a fourth input voltage. In this embodiment, the method further comprises determining the first input voltage when each of the first switch, the second switch, and the third switch are turned off (which once again results in no value for the first input voltage), determining the second input voltage when the first switch is turned on, and when both the second switch and the third switch are turned off, determining the third input voltage when the second switch is turned on, and when both the first switch and the third switch are turned off, and determining the fourth input voltage when both the first switch and the third switch are turned on, and when the second switch is turned off.

In this embodiment, the at least one output voltage comprises a first output voltage, a second output voltage, a third output voltage, and a fourth output voltage. The first output voltage is determined using the first input voltage, the offset voltage, and a gain of the receiver device, the second output voltage is determined using the second input voltage, the offset voltage, and the gain of the receiver device, the third output voltage is determined using the third input voltage, the offset voltage, and the gain of the receiver device, and the fourth output voltage is determined using the fourth input voltage, the offset voltage, and the gain of the receiver device.

In one embodiment, the method further comprises amplifying the at least one output voltage prior to determining the thermistor resistance and dithering the at least one amplified output voltage, wherein the at least one amplified output voltage is used to determine the thermistor resistance. In this embodiment, the dithering step further comprises applying a plurality of small voltages to the amplified output voltage. The plurality of small voltages cover a range of a predetermined least significant bit (LSB) of an analog-to-digital converter (ADC). In one embodiment, the predetermined LSB is 1 LSB of the ADC.

In one embodiment, a system for determining thermistor resistance comprises a temperature sensor network embedded within temperature sensor of a wireless sensor device. The temperature sensor network includes a driver device and a receiver device. The system further comprises a dual bond wire system that couples the driver device to the receiver device, wherein at least one output voltage is determined using at least one input current flowing through the dual bond wire system, further wherein the thermistor resistance is determined using the at least one output voltage. In this embodiment, the dual bond wire system comprises a first set of bond wires coupled to the driver device and a second set of bond wires coupled to the receiver device, further wherein the at least one input current passes through the first set of bond wires but does not pass through the second set of bond wires.

As above described, a system and method in accordance with the present invention utilizes a temperature sensor circuit/network within a temperature sensor of a wireless and wearable sensor device to provide an improvement in the wireless sensor device's capability of accurately determining the resistance of the thermistor. The accurate determination of the thermistor's resistance enables more accurate and consistent user body temperature monitoring by the wireless sensor device thereby improving the technical field related to health-related monitoring of users using wearable sensor devices. The temperature sensor circuit utilizes a dual bond wire configuration and circuitry design (comprising a first and a second set of bond wires) between the driver and receiver units to eliminate errors in the resistance measurements.

By separating the bond wires in this fashion, the current from the driver is passed through the first set of bond wires, but the receiver measuring the voltage drop of the resistors (the thermistor and the reference resistor) does not measure the voltage drop of the first set of bond wires which leads to more accurate resistance measurements because the second set of bond wires attached to the receiver will not have any current running through it which doesn't affect the captured voltage. The various output voltages (depending on whether a two-step or four-step process is utilized) from the receiver are calculated and the total resistance of the thermistor is determined by the wireless sensor device using these output voltages. In addition, a dithering unit and process can be utilized to further reduce noise associated with the captured output voltages and analog signal before it is digitized by the ADC.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for determining thermistor resistance, the method comprising:
   providing a temperature sensor network within a wireless sensor device, wherein the temperature sensor network includes a driver device and a receiver device;
   coupling the driver device to the receiver device using a dual bond wire system;
   separating the dual bond wire system into a first set of bond wires and a second set of bond wires;
   connecting each of the first set of bond wires and the second set of bond wires between a pin of a chip package and a pad on a chip die utilizing two pads per pin, wherein the first and second set of bond wires connect to the same pin of the chip package of the temperature sensor;
   sending current through the first set of bond wires of the dual-bond wire;
   determining at least one output voltage using at least one input current flowing through the dual bond wire system excluding the voltage through the first set of bond wires;
   amplifying the at least one output voltage;
   dithering the at least one amplified output voltage by applying a plurality of small voltages to the at least one amplified output voltage wherein the plurality of small voltages cover a range of a predetermined least significant bit (LSB) of an analog-to-digital converter (ADC) used for digitization; and
   determining the thermistor resistance using the at least one output voltage.

2. The method of claim 1, wherein the determining of the least one output voltage is done prior to digitization by the analog-to-digital converter (ADC) coupled to the receiver device.

3. The method of claim 1, wherein the dual bond wire system comprises a first set of bond wires coupled to the driver device and a second set of bond wires coupled to the receiver device, further wherein the at least one input current passes through the first set of bond wires but does not pass through the second set of bond wires.

4. The method of claim 3, wherein one of the first set of bond wires is coupled to one of the second set of bond wires and the other of the first set of bond wires is coupled to the other of the second set of bond wires.

5. The method of claim 3, further comprising:
determining an input voltage using a plurality of switches across the first set of bond wires and measuring an offset voltage across the second set of bond wires.

6. The method of claim 5, wherein the plurality of switches comprises a first switch, a second switch, and a third switch.

7. The method of claim 6, wherein the input voltage comprises a first input voltage and a second input voltage.

8. The method of claim 7, further comprising:
determining the first input voltage when each of the first switch, the second switch, and the third switch are turned off; and
determining the second input voltage when both the first switch and the third switch are turned on, and when the second switch is turned off.

9. The method of claim 8, wherein the at least one output voltage comprises a first output voltage and a second output voltage.

10. The method of claim 9, wherein the first output voltage is determined using the first input voltage, the offset voltage, and a gain of the receiver device and the second output voltage is determined using the second input voltage, the offset voltage, and the gain of the receiver device.

11. The method of claim 6, wherein the input voltage comprises a first input voltage, a second input voltage, a third input voltage, and a fourth input voltage.

12. The method of claim 11, further comprising:
determining the first input voltage when each of the first switch, the second switch, and the third switch are turned off;
determining the second input voltage when the first switch is turned on, and when both the second switch and the third switch are turned off;
determining the third input voltage when the second switch is turned on, and when both the first switch and the third switch are turned off; and
determining the fourth input voltage when both the first switch and the third switch are turned on, and when the second switch is turned off.

13. The method of claim 12, wherein the at least one output voltage comprises a first output voltage, a second output voltage, a third output voltage, and a fourth output voltage.

14. The method of claim 13, wherein the first output voltage is determined using the first input voltage, the offset voltage, and a gain of the receiver device, the second output voltage is determined using the second input voltage, the offset voltage, and the gain of the receiver device, the third output voltage is determined using the third input voltage, the offset voltage, and the gain of the receiver device, and the fourth output voltage is determined using the fourth input voltage, the offset voltage, and the gain of the receiver device.

15. The method of claim 1, wherein the predetermined LSB is 1 LSB of the ADC.

16. A system for determining thermistor resistance, the system comprising:
a temperature sensor network within a wireless sensor device, wherein the temperature sensor network includes a driver device and a receiver device;
a dual bond wire system that couples the driver device to the receiver device,
wherein the dual bond wire system includes a first set of bond wires and a second set of bond wires,
wherein the first set of bond wires and the second set of bond wires are connected between a pin of a chip package and a pad on a chip die utilizing two pads per pin, wherein the first and second set of bond wires connect to the same pin of the chip package of the temperature sensor, and
wherein the driver device sends current through the first set of bond wires of the dual-bond wire, and the receiver device determines at least one output voltage using at least one input current flowing through the dual bond wire system excluding the voltage through the first set of bond wires;
an amplifier unit, wherein the amplifier unit amplifies the at least one output voltage; and
a dithering device, wherein the dithering device dithers the at least one amplified output voltage by applying a plurality of small voltages to the at least one amplified output voltage wherein the plurality of small voltages cover a range of a predetermined least significant bit (LSB) of an analog-to-digital converter (ADC) used for digitization;
wherein the thermistor resistance is determined using the at least one output voltage.

17. The system of claim 16, wherein the dual bond wire system comprises a first set of bond wires coupled to the driver device and a second set of bond wires coupled to the receiver device, further wherein the at least one input current passes through the first set of bond wires but does not pass through the second set of bond wires.

* * * * *